United States Patent [19]

Neward

[11] Patent Number: 5,019,086
[45] Date of Patent: May 28, 1991

[54] MANIPULABLE VACUUM EXTRACTOR FOR CHILDBIRTH AND METHOD OF USING THE SAME

[76] Inventor: Theodore C. Neward, 521 Scripps Dr., Claremont, Calif. 91711

[21] Appl. No.: 566,484

[22] Filed: Aug. 13, 1990

Related U.S. Application Data

[63] Continuation of Ser. No. 405,958, Sep. 12, 1989, abandoned.

[51] Int. Cl.5 .............................................. A61B 17/42
[52] U.S. Cl. .................................................. 606/123
[58] Field of Search ......................... 606/122, 123, 124

[56] References Cited

U.S. PATENT DOCUMENTS

| | | | |
|---|---|---|---|
| 3,202,152 | 8/1965 | Wood et al. | 606/123 |
| 3,592,198 | 7/1971 | Evans | 606/124 |
| 3,765,408 | 10/1973 | Kawai | 606/123 |
| 4,512,347 | 4/1985 | Uddenberg | 606/124 X |
| 4,730,617 | 3/1988 | King | 606/123 |

OTHER PUBLICATIONS

J. A. Chalmers, *The Venthouse the Obstetric Vacuum Extractor*, Year Book Medical Publishers, Chicago (1971), pp. 18-31.

Primary Examiner—Michael H. Thaler
Attorney, Agent, or Firm—Lyon & Lyon

[57] ABSTRACT

An improved vacuum extractor for childbirth including a cup portion with an elongated stem joined thereto. A portion of the elongated stem adjacent to the cup portion is provided with additional flexibility to allow bending of the elongated stem at the point of flexibility thereby permitting the cup to be folded into a position substantially parallel to the elongated stem thereby facilitating insertion into the birth canal. In a preferred embodiment; a separate handle piece is attachable to an end of the elongated stem opposite to the cup portion.

8 Claims, 1 Drawing Sheet

U.S. Patent    May 28, 1991    5,019,086
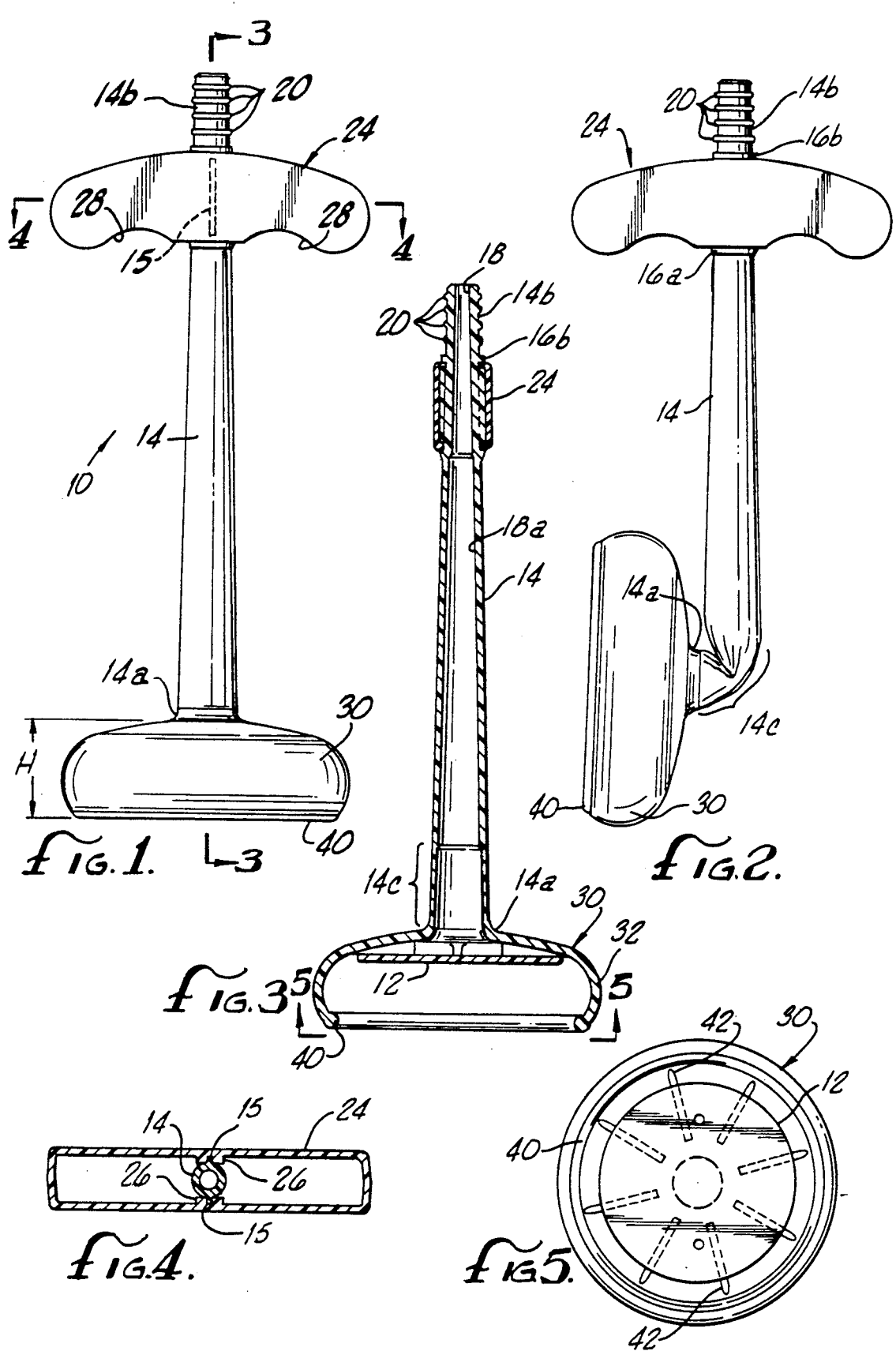

MANIPULABLE VACUUM EXTRACTOR FOR CHILDBIRTH AND METHOD OF USING THE SAME

This is a continuation of co-pending application Ser. No. 0 /405,958, filed on Sept. 12, 1989, now abandoned and which designated the U.S.

BACKGROUND OF THE INVENTION

The field of the present invention relates to an apparatus facilitating the extraction of a child during childbirth.

In some instances during childbirth, a completely natural birth is not possible and assistance must be rendered by the attending physician in order for the child to be delivered. Such assistance may be rendered with forceps and other similar devices, but these devices tend to be bulky and difficult to operate and their use introduces some chance of injury or discomfort to the mother and child. An alternative to forceps is a vacuum extractor device which uses a vacuum cup for attachment onto the head of the child. Joined to the cup is an elongated stem which is used to manipulate the cup. The physician may then apply a pulling force, accompanied by the proper positioning, to be transmitted to the child's head by manipulation of the stem of the device.

An existing obstetrical vacuum extractor is disclosed in U.S. Pat. No. 3,202,152. That patent describes a vacuum operated device, more specifically a vacuum cup, for attaching to the head of a child, an elongated stem joined to the cup which is used to manipulate the cup thereby enabling a pulling force to be applied to the child's head. Although that patent describes an effective vacuum extractor, the device can be difficult to manipulate into position onto the child's head.

Another existing vacuum extractor is the Malmstrdm device which has a vacuum cup with a rubber tube attached thereto. A vacuum is applied to the cup through the rubber tube. A chain is attached at one end to the cup and runs through the tube where it may be grasped by the physician in order to extract the cup. The Malmstrom device can only apply a pulling force and does not provide the physician with control to manipulate the child's head.

SUMMARY OF THE INVENTION

The present invention is directed to an improved vacuum extractor for childbirth including a cup portion with an elongated stem joined thereto. The vacuum extractor is designed to facilitate positioning onto the head of the child by improved manipulability. To this end a portion of the elongated stem, adjacent to the point where the stem joined to the cup portion, is provided with additional flexibility to allow bending of the elongated stem at the point of flexibility permitting the cup to be folded into a position substantially parallel to the elongated stem thereby facilitating insertion into the birth canal. In a preferred embodiment, a separate handle piece is attachable to an end of the elongated stem opposite to the cup portion.

BRIEF DESCRIPTION OF THE DRAWINGS

FIG. 1 is a front elevation view of an extractor according to the present invention;

FIG. 2 is a front elevation view of the extractor shown in FIG. 1 having the cup portion folded parallel to the elongated stem;

FIG. 3 is a cross-sectional view of the handle of FIG. 1 taken along line 3—3;

FIG. 4 is a cross-sectional view of the handle of FIG. 1 taken along line 4—4; and FIG. 5 is a view looking upward from the base of the extractor as in FIG. 3 along line 5—5.

DETAILED DESCRIPTION OF THE PREFERRED EMBODIMENT

The preferred embodiment will now be described with reference to the drawing. For convenience, any numeral identifying an element in one figure will represent the same element in any other figure.

The present invention provides improvement over the extractor disclosed in U.S. Pat. No. 3,202,152, the disclosure of which is hereby incorporated by reference. FIGS. 1-5 illustrate a vacuum extractor 10 comprised of an elongated hollow stem 14 which is joined at its front end 14a to the closed rear side of a cup portion 30. The stem 14 includes an opening 18 at a stem rear end 14b which permits communication between the hollow interior 18a of stem 14 and the interior of the cup 30 as best illustrated in the cross-sectional view of FIG. 3. A flexible hose (not shown) may be placed over the rear end 14b to provide a source of vacuum through stem 14 to the cup 30. To ensure an air-tight connection with the vacuum hose, the stem end 14b is provided with ribs or sealing rings 20 which are positioned circumferentially about the stem end 14b.

The cup portion 30 preferably has a bowl shape having a ridge 40 with a smooth or rounded contour around the outer rim of the open end thereof. The cup 30 has an outwardly rounded side 32 such that the internal diameter of the cup 30 at the ridge 40 is less than the internal diameter of the cup 30 at a midpoint of the side 32 of the cup 30 between its closed end and its open end.

The ridge 40 on the open end of the cup 30 has a smooth, rounded contour to provide a gentle and effective contact with the scalp of the child.

The stem 14 includes a flexible portion 14c adjacent the cup 30. The wall thickness of the stem 14 at the flexible portion 14c is reduced to provide such enhanced flexibility. As such, the cup 30 may be bent or folded to a position parallel to the stem 14, the stem 14 flexing at the flexible portion 14c, as shown in FIG. 2. By orienting the cup 30 as viewed in FIG. 2, the physician may more readily insert the extractor 10 into the birth canal. Once brought into position, the cup 30 may be released, the device will unfold and reorient the mouth 40 (back into a position as in FIG. 1) allowing the mouth 40 to be placed in contact with the child's scalp.

Positioning the flexible portion 14c adjacent the cup 30 allows the physician to minimize the total diameter of the object being inserted into the birth canal. Having a minimized total diameter or cross section in the folded condition enables the device to be inserted higher into the birth canal than other extraction instruments. Though flexible, the flexible portion 14c is designed to have memory and retain a desired amount of stiffness when it returns to the unflexed position. Proper amount of stiffness relative to the flexibility permits the desired bending characteristic shown in FIG. 2 while providing the desired stiffness for the physician to manipulate the device and guide the head of the child. The flexibility of the flexible portion may be accomplished by a reduced wall thickness. As an example, the thickness over most of the length of stem 14 is about twice the thickness at the stem flexible portion 14c, about 0.06" and 0.03" respectively.

The axial length or height "H" of the bowl shaped cup 30 is also reduced to minimize the outer dimension of the device in the folded condition when it is being inserted.

The cup 30 may have a series of reenforcing ribs 42 which are equally spaced about the interior of the cup 30 and extend longitudinally from near the mouth 40 toward the opening at the stem front end 14a. The cup 30 is also provided with a vacuum distributor member 12 which covers the entry from cup 30 to stem 14 to protect the baby's scalp from suction at the opening of the stem rear end 14a and to distribute the vacuum applied over an enlarged area on a child's scalp. The details of the distributor 12 are described in U.S. Pat. No. 3,202,152.

The present invention also includes an improved handle design for the extractor 10. The handle 24 is preferably comprised of separately molded halves which are attachable to the stem 14 near the stem rear end 14b. One of the two halves has eight posts which align with and snap into eight corresponding holes in the other half so that halves may be assembled in a snap fit arrangement. The stem 14 has one or more longitudinal guides 15 protruding outward from the surface of the stem 14, the handle 24 having internal grooves 26 corresponding thereto such that the grooves 26 mate with the longitudinal guides 15 providing a fit therebetween such that, when in position, the handle 24 does not rotate relative to the stem 14. The stem 14 includes a bottom stop 16a and a top stop 16b. To assemble, the two halves of the handle 24 are snapped together about the stem 14 between the stops 16a and 16b and then sonic welded in place.

The above-described construction enables the handle 24 and the stem 14/cup 30 portions to be separately molded. The handle 24 includes curved grooves 28 on side nearest the cup 30 to accommodate positioning of fingers of the physician thereagainst. The handle 24 may be made of a hard plastic thereby providing a stiffer grip surface to provide for more firm manipulation. The cup 30 and the stem 14 of the extractor 10 are preferably injection molded in a single mold from a plastic or plastic-like material such as low density polyethylene to provide a stiff yet reasonably flexible structure. This combination of properties permits the physician to manipulate the extractor 10 and guide the child's head through the birth canal.

Thus, an improved vacuum extractor for childbirth which provides greater manipulation and is readily constructed has been disclosed. While embodiments and applications of this invention have been shown and described, it will become apparent to those skilled in the art that other modifications are possible without departing from the inventive concepts herein. The invention, therefore, is not to be restricted except in the spirit of the claims that follow.

What is claimed is:

1. A vacuum extractor for childbirth comprising:
    a copy with an open front portion and a rear portion;
    a stem with a hollow interior and a front end and a rear end, the front end being attached to the rear portion of the cup with the interior of the cup communicating with the hollow interior of the stem,
    wherein a first portion of the front end of the stem adjacent the cup has greater flexibility than the rest of the stem, the first portion being sufficiently flexible to permit temporary bending of the stem to position the cup parallel to the stem for facilitating insertion into the birth canal and wherein the stem has sufficient stiffness (a) to return to an original unbent position when released and (b) to allow a physician to manipulate the extractor and apply a torque to and guide the child's head.

2. A vacuum extractor according to claim 1 further comprising
    a handle attachable to the rear end of the stem.

3. A vacuum extractor according to claim 1 wherein the cup and the stem are of a one-piece construction out of plastic or plastic-like material of suitable stiffness.

4. A vacuum extractor according to claim 1 wherein the flexible portion comprises a section of the stem adjacent the cup, the section having a reduced wall thickness.

5. A vacuum extractor for childbirth comprising:
    a cup with an open front portion and a rear portion;
    a stem with a hollow interior and a front end and a rear end, the front end being attached to the rear portion of the cup with the interior of the cup communicating with the hollow interior of the stem, the stem including a first flexible portion at the front end adjacent the cup, the first flexible portion having greater flexibility than the rest of the stem to permit temporary bending of the stem to position the cup parallel to the stem for facilitating insertion into the birth canal; and
    a handle attachable to the rear end of the stem,
    wherein the stem has sufficient stiffness (a) to return to an original unbent position when released and (b) to allow a physician to manipulate the extractor and apply a torque to and guide the child's head.

6. A vacuum extractor according to claim 5 wherein the cup and the stem are of a one-piece construction out of a plastic or plastic-like material of suitable stiffness.

7. A vacuum extractor according to claim 5 wherein the flexible portion comprises a section of the stem adjacent the cup with a reduced wall thickness.

8. A method for assisting in the extraction of a child during childbirth comprising the steps of:
    connecting a vacuum extractor to a vacuum applying device, the vacuum extractor including: (1) a cup portion with an open front portion and a rear portion, (2) a stem with a hollow interior and a front end and a rear end, the front end being attached to the rear portion of the cup portion with the interior of the cup portion communicating with the hollow interior of the stem, the stem including a flexible portion at the front end adjacent the cup portion to permit temporary bending the stem to position the cup portion parallel to the stem, and (3) a handle attached to the rear end of the stem;
    bending the stem at a point adjacent to the cup portion and positioning the cup portion parallel to the stem;
    inserting the cup portion in the bent condition to a desired position in the birth canal;
    releasing the cup portion and allowing the cup portion to return to its original position perpendicular to the stem;
    positioning the cup portion to the child's head;
    activating the vacuum applying device to apply a suction to the child's head; and
    grasping the handle and manipulating the extractor and the child's head to maneuver the child down the birth canal.

* * * * *

UNITED STATES PATENT AND TRADEMARK OFFICE
CERTIFICATE OF CORRECTION

PATENT NO. : 5,019,086

DATED : May 28, 1991

INVENTOR(S) : Theodore C. NEWARD

It is certified that error appears in the above-identified patent and that said Letters Patent is hereby corrected as shown below:

In column 1, line 37, the word "Malmstrdm" should read --Malmström--.

In column 3, line 59, the word "copy" should read --cup--.

Signed and Sealed this

Twenty-second Day of June, 1993

Attest:

MICHAEL K. KIRK

*Attesting Officer*  *Acting Commissioner of Patents and Trademarks*